United States Patent
Urban et al.

(10) Patent No.: US 12,408,955 B2
(45) Date of Patent: Sep. 9, 2025

(54) ADAPTER FOR PATIENT REFERENCE ARRAY AND BONE ANCHOR ASSEMBLY

(71) Applicant: NuVasive, Inc., San Diego, CA (US)

(72) Inventors: Matthew Urban, Denver, CO (US); Christopher Besaw, San Diego, CA (US); Andrew Wood, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 18/145,448

(22) Filed: Dec. 22, 2022

(65) Prior Publication Data

US 2023/0200864 A1 Jun. 29, 2023

Related U.S. Application Data

(60) Provisional application No. 63/294,229, filed on Dec. 28, 2021.

(51) Int. Cl.
*A61B 17/70* (2006.01)

(52) U.S. Cl.
CPC .................. *A61B 17/7083* (2013.01)

(58) Field of Classification Search
CPC .............. A61B 17/7077; A61B 17/708; A61B 17/7083; A61B 17/17086
See application file for complete search history.

(56) References Cited

U.S. PATENT DOCUMENTS

| | | |
|---|---|---|
| 6,190,395 B1 | 2/2001 | Williams |
| 6,226,548 B1 | 5/2001 | Foley et al. |
| 6,236,875 B1 | 5/2001 | Bucholz et al. |
| 6,711,431 B2 | 3/2004 | Sarin et al. |
| 6,856,828 B2 | 2/2005 | Cossette et al. |
| 7,753,910 B2 | 7/2010 | Ritland |
| 7,835,778 B2 | 11/2010 | Foley et al. |
| 8,317,844 B2 | 11/2012 | Maier et al. |
| 8,986,349 B1 | 3/2015 | German et al. |
| 9,005,211 B2 | 4/2015 | Brundobler et al. |
| 9,585,700 B2 | 3/2017 | Wehrle et al. |
| 9,907,582 B1 | 3/2018 | Olea |
| 10,117,712 B2 | 11/2018 | Plassky et al. |
| 10,433,883 B2 | 10/2019 | DiVincenzo et al. |
| 10,449,006 B2 | 10/2019 | Dace |
| 10,463,404 B2 | 11/2019 | Wall et al. |
| 10,702,343 B2 | 7/2020 | Kozak et al. |
| 10,987,129 B2 | 4/2021 | Thommen et al. |
| 11,135,015 B2 | 10/2021 | Crawford et al. |
| 2006/0074445 A1* | 4/2006 | Gerber ............... A61B 17/7076 606/191 |
| 2008/0125788 A1* | 5/2008 | Cohen ................ A61B 17/7085 606/104 |
| 2012/0232377 A1 | 9/2012 | Nottmeier |
| 2013/0310942 A1* | 11/2013 | Abdou ............... A61B 17/7079 623/17.16 |
| 2015/0100091 A1 | 4/2015 | Tohmeh et al. |
| 2015/0150569 A1 | 6/2015 | van der Walt et al. |
| 2017/0065269 A1* | 3/2017 | Thommen ............. A61B 1/233 |

(Continued)

*Primary Examiner* — Eduardo C Robert
*Assistant Examiner* — Holly Joanna Lane

(57) ABSTRACT

An apparatus includes a reference array, a bone anchor, a receiver assembly coupled to the bone anchor, and an adapter axially locked with the receiver assembly. The adapter includes a proximal end coupled to the reference array and a distal end coupled to the receiver assembly.

20 Claims, 15 Drawing Sheets

(56) References Cited

U.S. PATENT DOCUMENTS

| | | | |
|---|---|---|---|
| 2017/0252114 A1* | 9/2017 | Crawford | A61B 17/7089 |
| 2018/0014862 A1* | 1/2018 | Raina | A61B 17/708 |
| 2018/0092699 A1* | 4/2018 | Finley | A61B 34/20 |
| 2019/0000372 A1 | 1/2019 | Gullotti et al. | |
| 2019/0069934 A1* | 3/2019 | Mickiewicz | A61B 17/0206 |
| 2019/0231435 A1 | 8/2019 | Zucker et al. | |
| 2019/0380750 A1 | 12/2019 | Morris | |
| 2020/0196996 A1 | 6/2020 | Isaacs | |
| 2020/0360091 A1 | 11/2020 | Murray et al. | |
| 2020/0367940 A1 | 11/2020 | Loftis et al. | |
| 2021/0000491 A1 | 1/2021 | Chappuis et al. | |
| 2021/0030443 A1 | 2/2021 | Scholl et al. | |
| 2021/0038350 A1 | 2/2021 | Otawa | |
| 2021/0137603 A1 | 5/2021 | Zucker et al. | |
| 2022/0087723 A1 | 3/2022 | Scholl et al. | |
| 2022/0175466 A1 | 6/2022 | Murray et al. | |

* cited by examiner

ADAPTER FOR PATIENT REFERENCE ARRAY AND BONE ANCHOR ASSEMBLY

CROSS REFERENCE TO RELATED APPLICATIONS

This application claims priority to U.S. Provisional Application No. 63/294,229, filed Dec. 28, 2021, which is incorporated herein by reference in its entirety for any and all purposes.

BACKGROUND

Spinal surgical procedures often include application of bone anchor assemblies (e.g., bone screw assemblies) that are connected by rigid spinal rods locked to each bone anchor assembly. The bone anchor assemblies can often include a bone anchor and a rod-housing component, which can be referred to as a "receiver" or "tulip", that is often coupled to the bone anchor in a manner that permits angular adjustability of the tulip relative to the bone anchor.

A noteworthy trend in the medical community is the move away from performing surgical procedures on the spine via traditional "open" techniques in favor of so-called "minimally invasive" or "minimal access" techniques. Open surgical techniques are generally undesirable in that they typically require large incisions with high amounts of tissue displacement to gain access to the surgical target site, which produces concomitantly high amounts of pain, lengthened hospitalization (increasing health care costs), and high morbidity in the patient population. Less-invasive surgical techniques (e.g., including minimal access and minimally invasive techniques) are gaining favor because they involve accessing the surgical target site via incisions of substantially smaller size with greatly reduced tissue displacement requirements. This, in turn, reduces the pain, morbidity, and cost associated with such procedures.

One disadvantage to performing minimally invasive surgery is the increased reliance on radiographic imaging to "see" the spinal target site, instruments, and implants during the surgery. While this increased exposure is generally negligible for the patient, over time and over multiple procedures on different patients, this increased exposure adds up for the surgeon and other operating room personnel. Systems and methods have been developed to reduce reliance on radiographic imaging during spine surgery. Once such system and method involve three-dimensional (3D) navigation systems that use positional tracking systems to track the position of implants and instruments relative to the spinal target site and present the surgeon with a representative image of the instrument superimposed on an image of the target site to indicate the position of the implant or instrument relative to the anatomical structures depicted in the image. (e.g. spinal target site). However, these systems have the disadvantages of generally requiring that reference markers be somehow fixed to the patient (e.g. anchoring a pin or other instrument into the patient's spine, thus causing additional trauma to the patient's anatomy), requiring input of pre-operative CT images into the system before or during the procedure, and/or requiring large, specialized, and expensive equipment that may not be available in certain instances or operating rooms. Furthermore, even though 3D navigation provides spatial information regarding a target surgical site, instruments, and implants during surgery, it does not provide neurophysiologic information regarding the nerves lying near and around the operative corridor.

There is a need for systems, methods, and apparatuses that address one or more shortcomings in the art and provide one or more advantages.

SUMMARY

A first example apparatus includes: a reference array, a bone anchor, a receiver assembly coupled to the bone anchor, and an adapter axially locked with the receiver assembly. The adapter includes a proximal end coupled to the reference array and a distal end coupled to the receiver assembly. The receiver assembly can include one or more tool engagers. The adapter can include one or more receiver assembly engagers coupled with the one or more tool engagers. The one or more receiver assembly engagers can include one or more arms. The receiver assembly can include at least two receiver arms defining a channel therebetween configured to receive a spinal rod. The adapter can include a channel engager configured to engage within the channel. The adapter can include a driver configured to advance the channel engager into the channel and withdraw the channel engager from the channel.

A second example apparatus includes a proximal end having a reference array coupler, a distal end defining an opening configured to receive a receiver assembly, and one or more receiver assembly engagers configured to engage with the receiver assembly.

The one or more receiver assembly engagers can include one or more arms biased into a locked position. The one or more arms can include one or more tabs configured to fit within one or more tool engagers of the receiver assembly. The channel engager can be configured to engage within a channel formed by the receiver assembly. The channel engager can include a channel engager shaft having a channel engager bar extending perpendicular to a length of the channel engager shaft. The channel engager bar can be the portion of the channel engager that engages within the channel. The channel engager bar can mimic a shape and diameter of a spinal rod. The driver can be configured to advance the channel engager into the channel and withdraw the channel engager from the channel. The driver can be configured as a lead screw configured to translate rotational force applied to the driver to advance or withdraw the channel engager.

An example method can include: coupling an adapter with a receiver assembly, coupling a reference array to a proximal end of the adapter, and adjusting an angle of a receiver assembly with respect to a bone anchor. The adjusting can simultaneously adjust an angle of the adapter with respect to the bone anchor.

The coupling of the adapter with the receiver assembly can include disposing one or more tabs of an arm of the adapter within one or more tool engagers of the receiver assembly. The method can further include, after adjusting the angle, advancing a channel engager of the adapter into a channel of the receiver assembly, thereby locking an angle of the receiver assembly with respect to the bone anchor. The method can further include advancing a channel engager of the adapter toward a channel of the receiver assembly such that the channel engager contacts a set screw or rod disposed in the receiver assembly. The method can be performed during a revision spinal surgery. The bone anchor may have been placed during a prior spinal surgery. The method can further include uncoupling the adapter from the receiver assembly and connecting the receiver assembly with another receiver assembly via a rod.

DETAILED DESCRIPTION

An example adapter is configured for attaching a reference array to a bone anchor assembly implanted in a patient. The attachment of the adapter facilitates the customizable directionality of the reference array during a navigated procedure, such as a spine procedure. Bone anchor assemblies used in spine procedures can include a component known as a "tulip" or "receiver", which is a component configured to receive and anchor a spinal rod. The adapter includes a distal end that is configured to connect with the tulip via two arms that fit into tool engagers of the tulip. The adapter can be coupled such that long axes of the adapter and the tulip are coaxial or at least parallel. Once connected, the reference array is pivotable about a head of a bone anchor to which the tulip is connected and with which the tulip has a polyaxial relationship. After pivoting the reference array (e.g., such that the reference array faces a camera of a surgical navigation system, an inner shaft of the adapter is driven into the tulip in a manner that locks the tulip head in place and creates a rigid construct.

In an example, the adapter is configured to couple with a single bone anchor assembly. In an example, the adapter is configured to couple with multiple bone anchor assemblies. In an example, the adapter lacks a feature configured to couple to a spinal rod.

Figure 1:
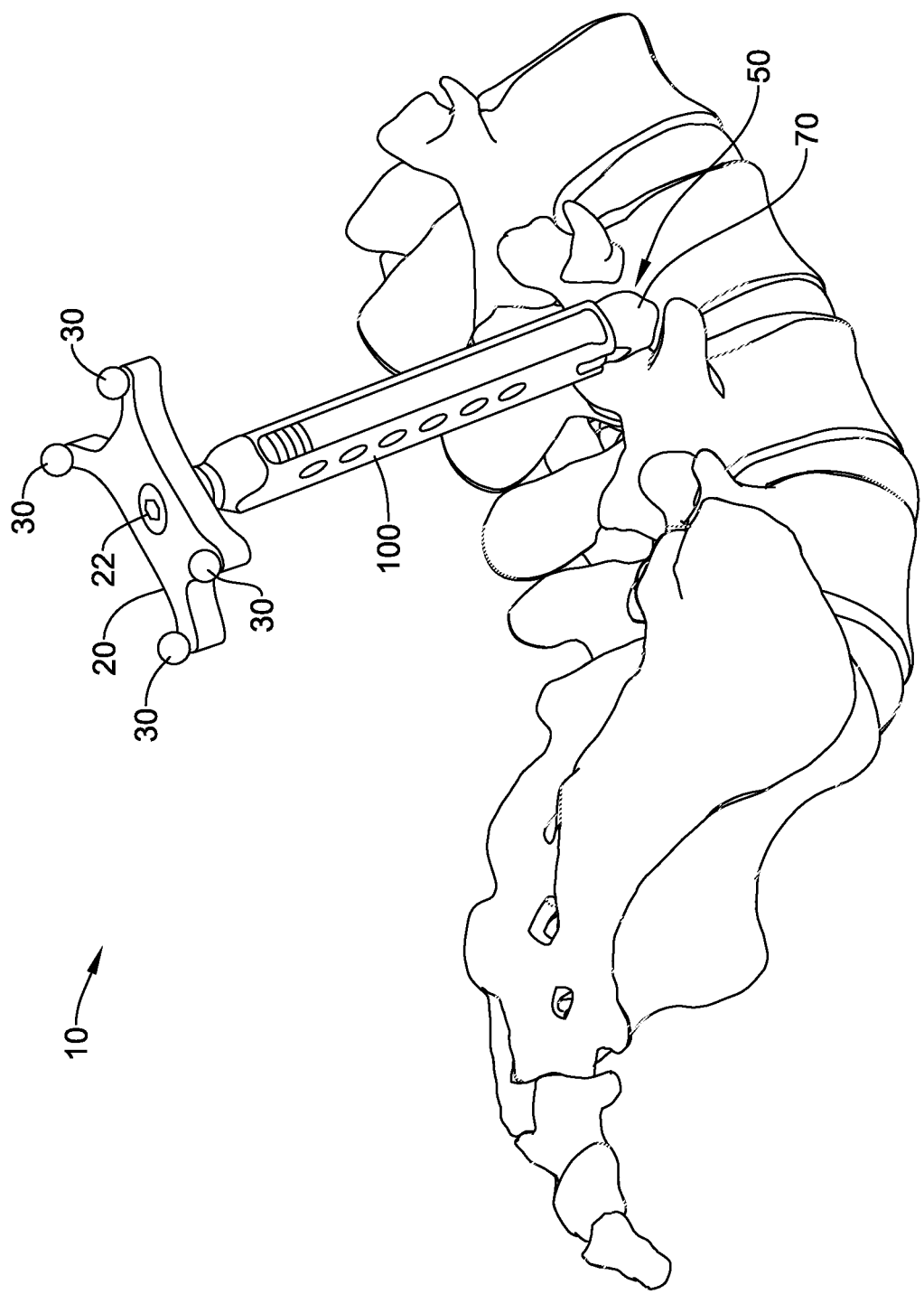
FIG. 1 illustrates, with respect to a patient's spine, an apparatus that includes a reference array coupled to a bone anchor assembly via an adapter.

An example implementation of an adapter with respect to a patient's spine is shown and described in relation to FIG. 1.

FIG. 1 illustrates, with respect to a patient's spine, an apparatus 10 that includes a reference array 20 coupled to an adapter 100 that is coupled to a bone anchor assembly 50.

The illustrated bone anchor assembly 50 includes a receiver assembly 70 coupled to a bone anchor 60 implanted in a pedicle of vertebra of the spine. The bone anchor assembly 50 can be configured the receiver assembly 70 is couplable to a polyaxial bone anchor (e.g., a pedicle screw).

The receiver assembly 70 can be initially movable relative to the bone anchor in a polyaxial fashion and subsequently lockable relative to the bone anchor (e.g., prior to or as part of locking a rod in the receiver assembly 70). Additional details regarding an example implementation of a bone anchor assembly 50 are provided in relation to FIG. 16. Bone anchor assemblies 50 can take any of a variety of forms and are commonly used in spinal procedures. Many implementations include a receiver assembly, collet, and bone anchor. Example implementations are described in US 2020/0367940, filed May 22, 2019, and U.S. Pat. No. 8,986,349, filed Nov. 12, 2010, both of which are incorporated herein by reference in their entirety for any and all purposes.

The illustrated reference array 20 includes one or more fiducials 30. The body of the reference array supports the one or more fiducials 30. The spacing, orientation, and other ways in which the fiducials 30 are disposed at the reference array can be used to convey meaning to a user or surgical navigation system. In the illustrated example, the fiducials 30 are passive infrared retroreflectors configured to reflect infrared light emitted by a tracking system back to the tracking system. In other examples, the fiducials 30 are active infrared emitters that actively emit infrared light. In still other examples, the fiducials 30 are some other object meaningful to implementing surgical navigation, such as the receiver or transmitter of energy used in tracking (e.g., ultrasonic energy or electromagnetic energy) or a visible light tracking glyph. In some examples, the reference array 20 includes a mix of types of fiducials (e.g., a mix of fiducials 30 configured to act in visible and infrared light).

The illustrated reference array 20 further includes a fastener 22 for coupling the reference array with the adapter 100. As illustrated, the fastener 22 is a threaded fastener that mates with threads of the adapter 100, but the fastener 22 can take any of a variety of forms, such as a snap fit fastener, bayonet coupler, a magnetic fastener, other kinds of couplers, or combinations thereof.

The adapter 100 is a component configured to facilitate coupling of the reference array 20 to a bone anchor assembly 50 and is described in more detail in figures herein.

Figure 2:
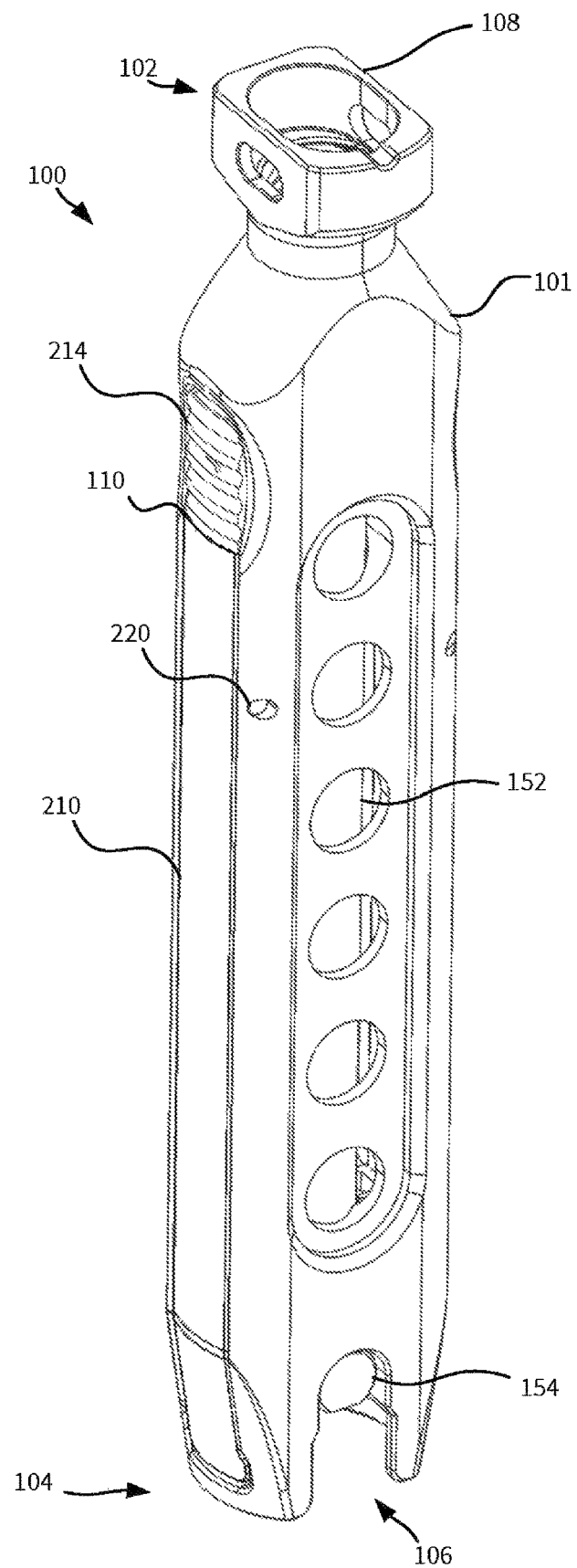
FIG. 2 illustrates a perspective view of the adapter.
Figures 3, 4:
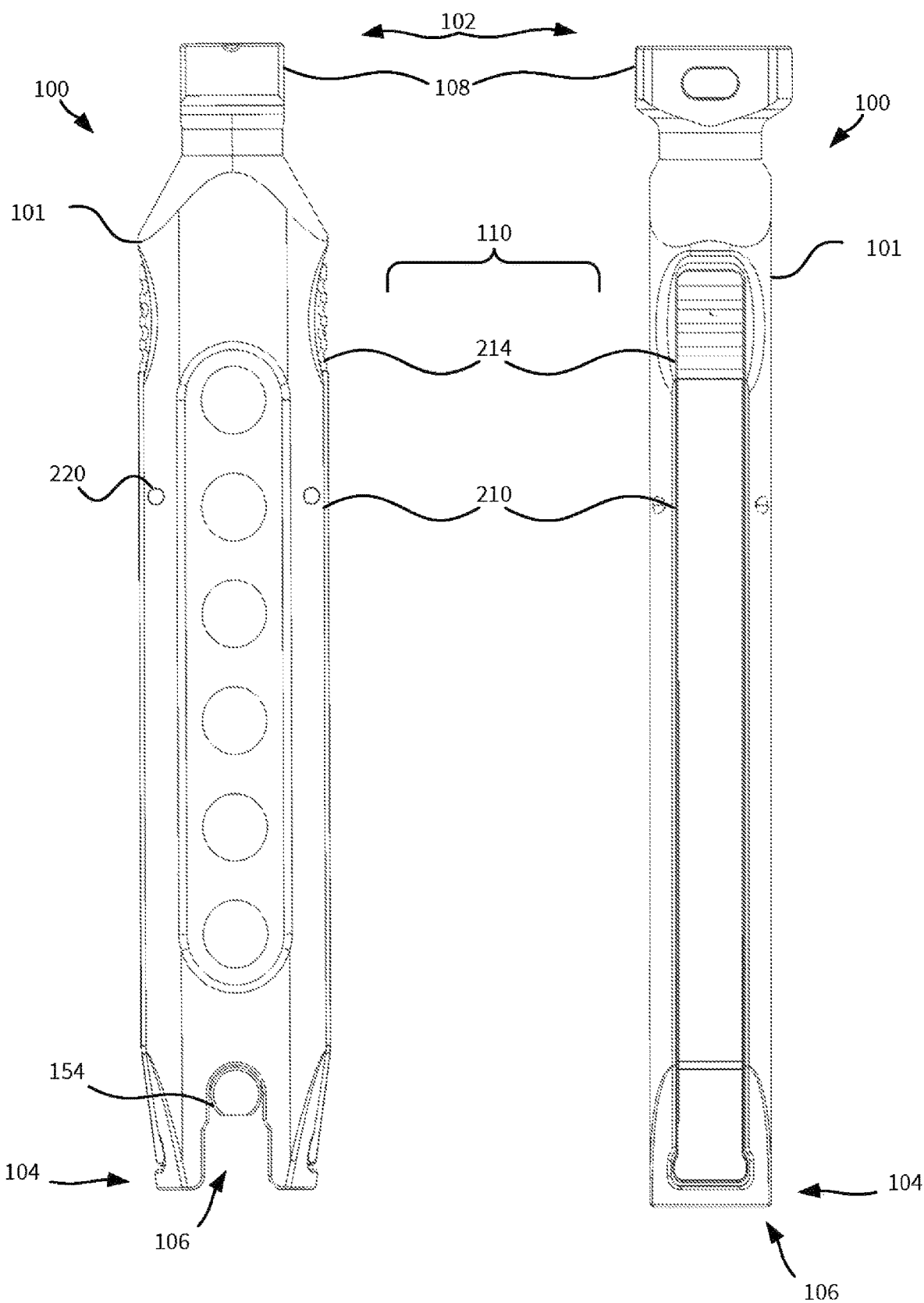
FIG. 3 illustrates a front view of the adapter.
FIG. 4 illustrates a side view of the adapter.
Figure 5:
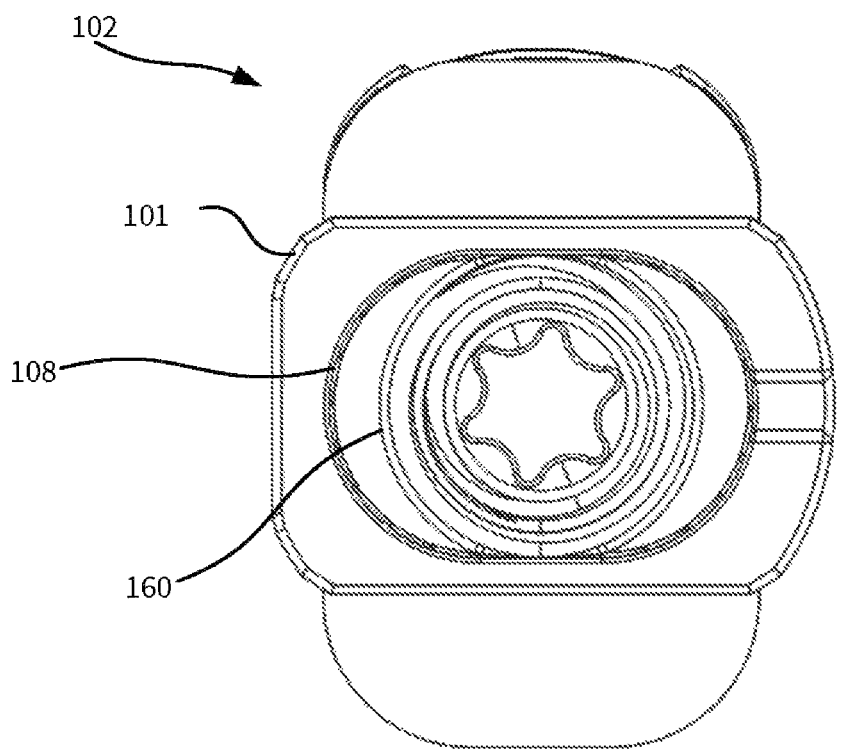
FIG. 5 illustrates a top view of the adapter.
Figure 6:
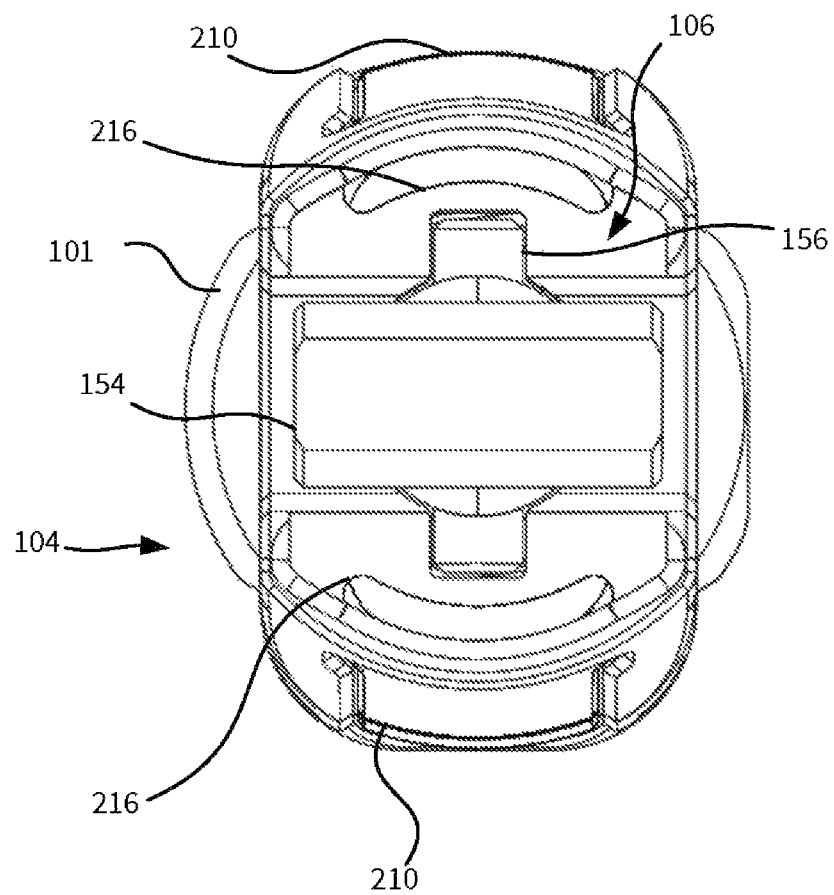
FIG. 6 illustrates a bottom view of the adapter.
Figure 7:
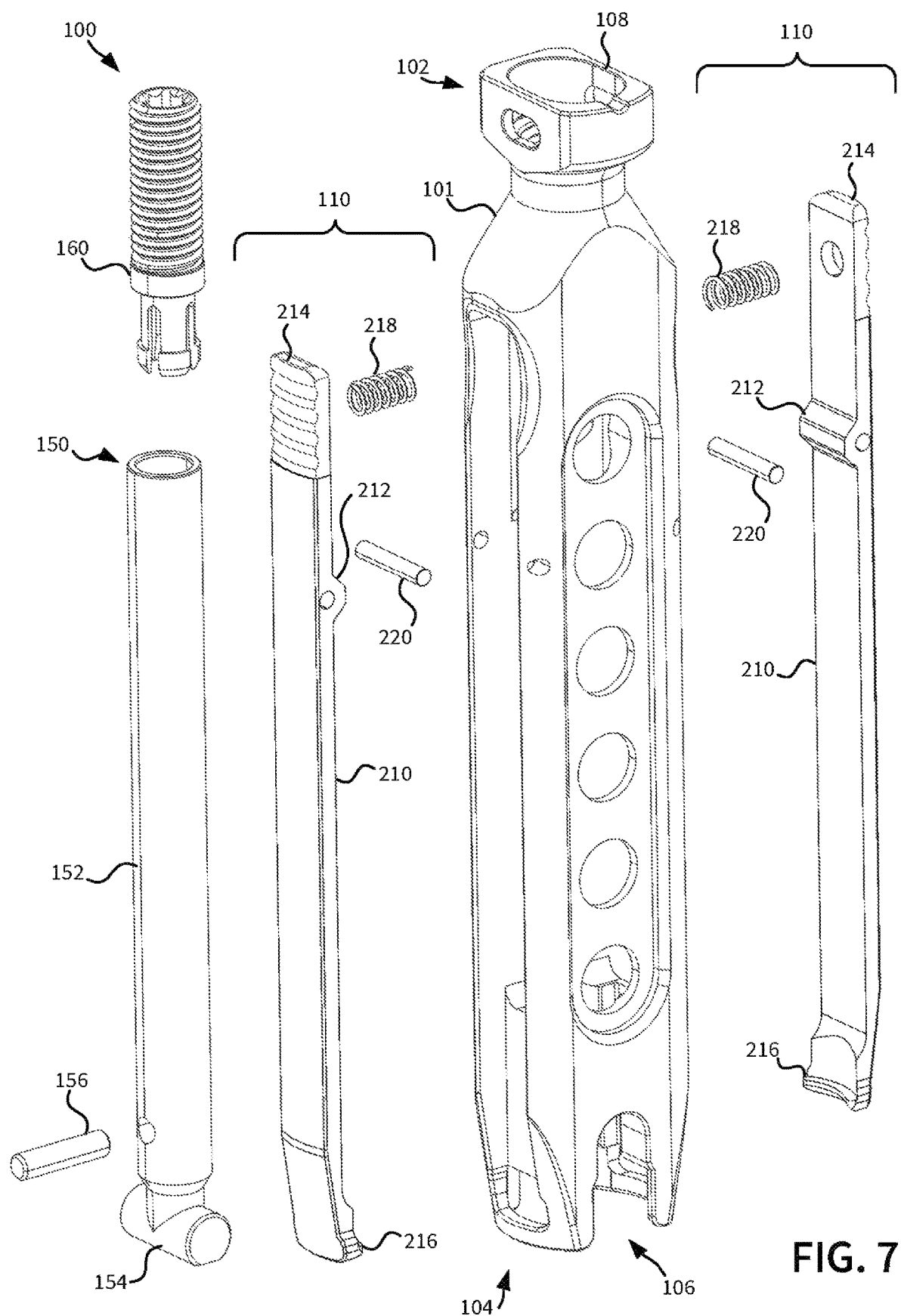
FIG. 7 illustrates an exploded view of the adapter.
Figure 8:
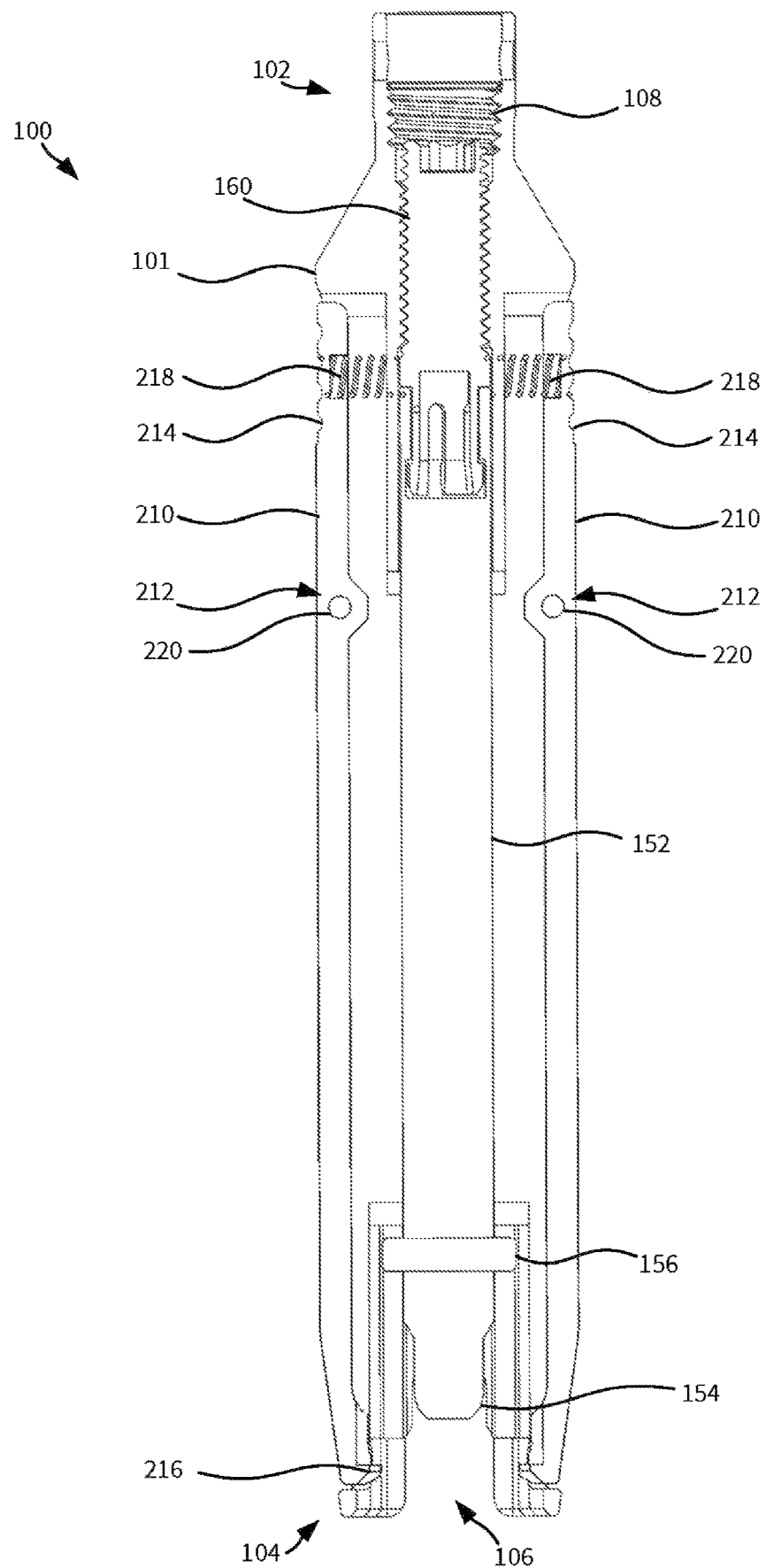
FIG. 8 illustrates a cutaway view of the adapter.

FIGS. 2-8 illustrate various views of an example implementation of the adapter 100. In particular, FIG. 2 illustrates a perspective view of the adapter 100. FIG. 3 illustrates a front view of the adapter 100. FIG. 4 illustrates a side view of the adapter 100. FIG. 5 illustrates a top view of the adapter 100. FIG. 6 illustrates a bottom view of the adapter 100. FIG. 7 illustrates an exploded view of the adapter 100. FIG. 8 illustrates a cutaway view of the adapter 100.

The adapter 100 includes a body 101 defining proximal end 102 and a distal end 104. At the proximal end 102, the body 101 defines a reference array coupler 108. At the distal end, the body 101 defines an opening 106. Coupled to the body 101 is at least one receiver assembly engager 110. The adapter 100 further includes a channel engager 150 that is driven by a driver 160.

Figure 10:
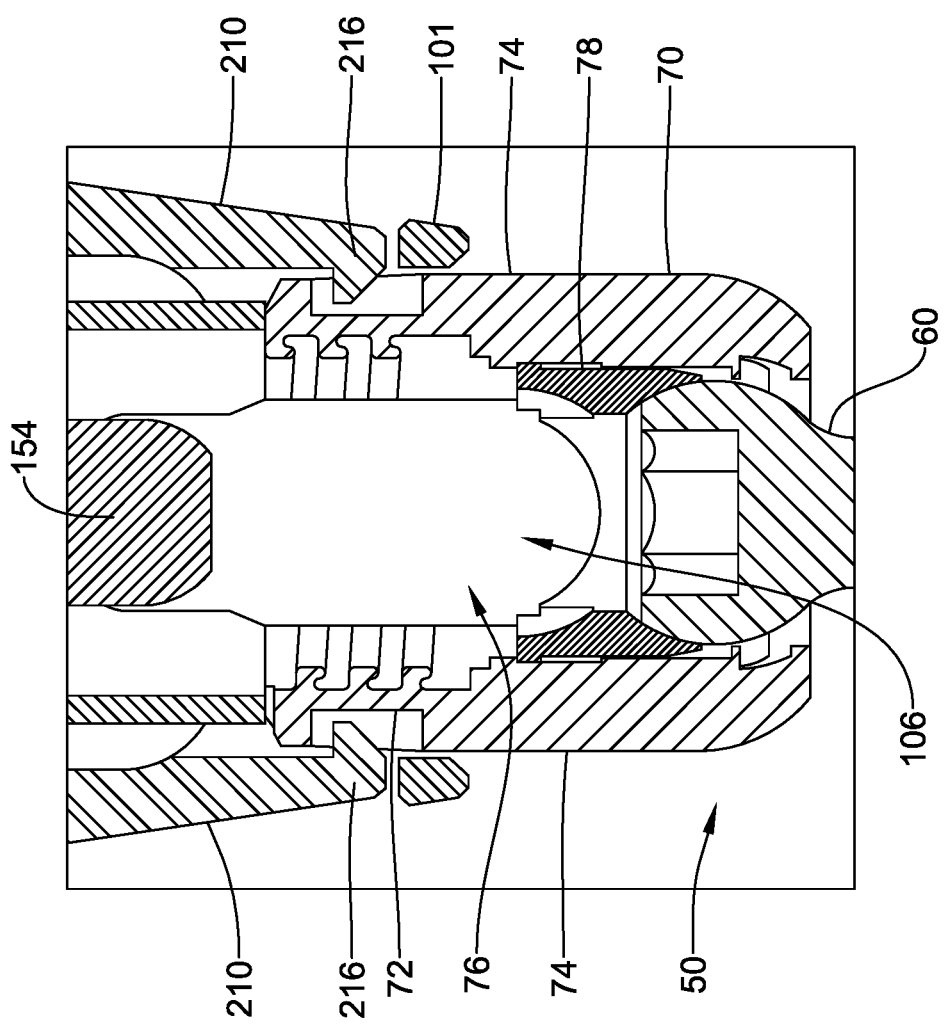
FIG. 10 illustrates a cutaway view of the adapter coupled to the bone anchor assembly.

The opening 106 can be sized and shaped to fit at least a portion of the receiver assembly 70. The portion of the receiver assembly 70 (e.g., a proximal end of the receiver assembly 70) can fit within the opening 106. The fit can be sufficiently tight as to permit relatively easy insertion of the receiver assembly 70 by a user while resisting lateral movement or tipping of the body 101 relative to the receiver assembly 70 once the receiver assembly 70 is sufficiently inserted within the opening 106. An example of the fit is shown in FIG. 10, which is discussed in more detail infra.

The reference array coupler 108 is a portion of the adapter 100 configured to couple with a reference array 20. The reference array coupler 108 can couple via any of a variety of kinds of mechanisms. For example, the illustrated example of the reference array coupler 108 has threads for coupling with threads of the screw fastener 22 for securing the reference array 20. In other implementations, the reference array coupler 108 can have other kinds of mechanisms for coupling, such as a snap fit fastener, bayonet coupler, a magnetic fastener, other kinds of couplers, or combinations thereof. In addition, the overall shape of the reference array coupler 108 can facilitate coupling with the reference array 20. As illustrated, the reference array coupler 108 can fit within a portion of the reference array 20 to resist movement of the reference array 20 with respect to the reference array coupler 108 in at least one direction.

In the illustrated example, the reference array coupler 108 is in a fixed relationship with the body 101, such that the angle of the reference array coupler 108 or a reference array 20 coupled thereto cannot be adjusted relative to the body 101. In other examples, the reference array coupler 108 or the reference array 20 coupled thereto is adjustable relative to the body 101. For example, the body 101 may define a central axis along the length of the body (e.g., from proximal end 102 to distal end 104) and the angle along which the reference array 20 couples to the coupler 108 can be adjusted relative to the central axis. Various adjustment mechanisms can be used, such as via one or more articulating joints.

The receiver assembly engager 110 is a mechanism of the adapter 100 configured to couple with a receiver assembly 70. The arrangement of the receiver assembly engager 110 can vary depending on the arrangement of the receiver assembly 70. In an example, the receiver assembly 70 includes a tool engager (e.g., a groove, detent, or other feature configured to couple with a rod inserter or other instrument) and the receiver assembly engager 110 is configured to couple thereto. An example implementation is illustrated.

In the illustrated example, the adapter 100 has two receiver assembly engagers 110. Each receiver assembly engager includes an arm 210 having an arm interface 214 at a proximal end and a tab 216 at a distal end. The arm 210 further includes an arm pivot 212 and the arm 210 engages with an arm spring 218.

The arm 210 is an elongate structure that supports or defines components useful in engaging with the receiver assembly 70. As illustrated, the arm 210 runs along an exterior of the adapter 100.

The arm interface 214 is a portion of the arm 210 configured to receive interaction from the user. For example, the arm interface 214 can be in the form of an area for the user to press to cause the arm 210 to rotate about the arm pivot 212 to cause the distal end of the arm 210 to move outward. This movement can be used to decouple the receiver assembly engager 110 from the receiver assembly 70. The arm interface 214 includes grooves or other features (e.g., knurling or coloring) to facilitate the interaction with the user.

The tab 216 is a portion configured to interact with the tool engager of the receiver assembly 70. In the illustrated example, the tab 216 extends inward from the arm 210 to fit within the tool engager of the receiver assembly and resist proximal movement of the adapter 100 relative to the receiver assembly 70. The tab 216 can extend from the arm 210 such that the tab 216 extends into the opening 106 to reach the receiver assembly 70 when the receiver assembly 70 is received within the opening 106. The tab 216 can include a ramped distal surface such that when the tab 216 is pushed distally onto the receiver assembly 70, the interaction therebetween causes the distal end of the arm 210 to be pushed outward. Continued pushing can result in the tab 216 falling (or being pushed) into the tool engager of the receiver assembly 70. A proximal end of the tab 216 can be flat, such that the proximal end of the tab 216 catches on the tool engager and resists proximal movement of the adapter 100 relative to the receiver assembly 70. Further details regarding this interaction is described in more detail in relation to FIG. 10.

In the illustrated example, the arms 210 end in tabs 216 and the tabs 216 are configured to interact with the tool engagers. In other examples, the arms 210 can include other components in addition to or instead of the tabs 216. The configuration of such components can vary depending on the kind of receiver assemblies 70 to which the adapter 100 is to be coupled.

The arm pivot 212 is a pivot portion about which the arm 210 pivots relative to the body 101. The arm pivot 212 can be coupled to the body 101 via an arm pin 220. In the illustrated example, the arm pivot 212 is an extended piece of material having a passage extending therethrough that accommodates an arm pin 220. In other implementations, the arm pivot 212 can be or include one or more features configured to interact with the body to facilitate pivoting or otherwise moving the arm 210 with respect to the body 101.

The arm spring 218 is a component of the adapter 100 that biases the arm 210 into a closed position. As illustrated, the arm spring 218 is disposed toward the proximal end of the arm 210 and pushes the proximal end outward such that the distal end of the arm 210 is urged inward. Such urging inward can encourage the tab 216 to fall into the tool engager and resist unwanted disengagement. In other implementations, in addition to or instead of an arm spring 218, other biasers can be used.

The channel engager 150 is a portion of the adapter 100 configured to engage with a channel of the receiver assembly 70. The illustrated channel engager 150 includes an elongate channel engager shaft 152 having, at its distal end, a channel engager bar 154. As illustrated, the channel engager shaft 152 is an elongate structure running parallel to and coaxial with the length of the body 101. As illustrated, the channel engager shaft 152 has a length less than a length of the body, but can have other lengths in other implementations. A channel engager pin 156 is coupled to the channel engager 150 and facilitates guiding the channel engager down a track in the body 101.

The illustrated channel engager bar 154 is an end effector of channel engager 150 that is configured to engage with the channel of the receiver assembly 70. In this example, the end effector is in the form of a channel engager bar 154. The bar 154 has a length that extends perpendicularly from a distal end of the channel engager shaft 152. As illustrated, the length of the bar 154 is not greater than a width of the body 101 (e.g., the width can be greatest width of the body 101 in a direction parallel to the length of the bar 154). The bar 154 can be sized and shaped to mimic a spinal rod that would be inserted into a channel of the receiver assembly. In addition or instead, the bar 154 can have a flat distal surface to facilitate interaction with a set screw, other flat feature of the receiver assembly 70, or a non-circular rod. In other examples, the bar 154 can have a convex distal surface to facilitate engagement between the bar 154 and a spinal rod already inserted in the receiver assembly. In many examples, the channel engager bar 154 is formed from a rigid material. In some examples, the channel engager bar is constructed from or includes a pliable material configured to facilitate grip between the channel engager 150 and the receiver assembly 70.

In other examples, the end effector of the channel engager 150 is not the illustrated bar and is a threaded component that mimics the size of a set screw that would be disposed in the receiver assembly 70 to, for example, lock a rod. As described elsewhere herein, the receiver assembly 70 can include threads or grooves configured to interface with a set screw. The end effector of the channel engager 150 can be configured to thread into these threads or grooves to interact with the receiver assembly.

The channel engager 150 can include or be configured to interact with (e.g., via a feature on a proximal end of the channel engager) a driver 160.

The driver 160 is a component configured to facilitate the advancement and retraction of the channel engager. In the illustrated example, the driver 160 is arranged as a leadscrew mechanism that pushes against the channel engager 150 as a feature of the driver 160 is advanced by a screwdriver. The driver 160 can be arranged with a distal feature that pulls on the channel engager 150 as the feature of the driver is retracted with a screwdriver. The proximal end of the driver 160 can include the feature that interacts with a screwdriver and the feature can be accessible through the proximal end of the adapter 100.

The adapter 100 can be used during a surgical procedure to facilitate navigation with the reference array 20.

Figure 9:
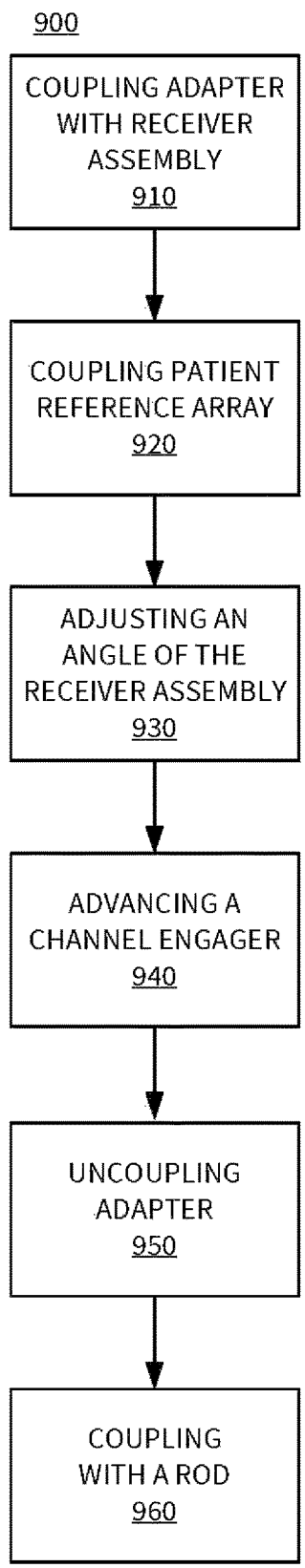
FIG. 9 illustrates an example method.

FIG. 9 illustrates an example method 900 of using the adapter 100. The method 900 can be performed during a surgery. In an example, the surgery can be a spinal surgery, such as a revision spinal surgery. The method 900 can include placing a bone anchor 60 or exposing a bone anchor 60 that was placed during a prior spinal surgery. In the illustrated example, the method 900 begins with operation 910.

Operation 910 includes coupling the adapter 100 with the receiver assembly 70. In an example, the operation 910 occurs while the receiver assembly 70 is coupled to bone anchor 60 that is anchored in bone. For example, the bone anchor 60 can be a bone screw anchored in a patient's pedicle, and the receiver assembly 70 is configured to receive a spinal rod. The operation 910 can be accomplished in any of a variety of ways depending on how the adapter 100 and receiver assembly 70 are arranged, such as via snapping, twisting, threading, ratcheting, other fastening actions, or combinations thereof. In an example, the coupling of the adapter 100 with the receiver assembly 70 includes disposing one or more tabs 216 of the one or more arms 210 of the adapter 100 within one or more tool engagers 72 of the receiver assembly 70. For instance, the opening 106 at the distal end 104 of the adapter 100 located over the receiver assembly 70 and pushed downward. As the adapter 100 is pushed downward, a ramped distal surface of the one or more tabs 216 contacts the proximal end of the receiver assembly 70 (e.g., a proximal end of the receiver arms 74) and causes the distal end of the arm 210 to be pushed outward. The user continues pushing the adapter 100 onto the receiver assembly 70, which results in the tab 216 falling into the tool engager of the receiver assembly 70, which results in the arrangement shown in FIG. 10. The tabs 216 can be inward facing such that they extend toward a central axis of the adapter 100.

FIG. 10 illustrates a cross-sectional view an example coupling between the adapter 100 and the receiver assembly 70. Here, the tabs 216 of the arms 210 have fallen into tool engagers 72 of receiver arms 74 of the receiver assembly 70.

As illustrated, the tool engagers 72 take the form of grooves in the receiver arms 74. While in this arrangement, proximal movement of the adapter 100 would be resisted by an interaction between the proximal flat surface of the tabs 216 and the proximal flat surfaces of the tool engagers 72. As can be further seen in this view, the fit between the opening of the adapter and the outer surface of the receiver assembly is sufficiently tight as to resist significant movement relative to the receiver assembly (e.g., movement that would cause accuracy errors outside of a tolerated range for a navigation system relying on a reference array 20 held by the adapter 100). As further illustrated, the bar 154 is in a retracted (e.g., undeployed) state, and a collet 78 of the bone anchor assembly 50 is in such a position as to not resist polyaxial movement of the receiver assembly 70 relative to the bone anchor 60. Additionally, the illustrated adapter 100 is advanced as far as possible onto the receiver 70 because a portion of the body 101 forming a portion of the proximal end of the opening 106 abuts the receiver 70 and prevents further advancement. The figure further shows that distal movement of the collet 78 (e.g., as a result of pressure from the bar 154) can cause the collet 78 to interact with the bone anchor 60 and the receiver assembly 70 so as to resist polyaxial movement of the receiver assembly 70 relative to the bone anchor 60.

Returning to FIG. 9, operation 920 includes coupling a reference array 20 to a proximal end of the adapter 100. The specific coupling method can vary depending on the specifics of the reference array 20 and the reference array coupler 108. The coupling can include snapping, twisting, threading, ratcheting, other fastening actions, or combinations thereof to make the connection. An example connection between the reference array 20 and the reference array coupler 108 is shown in FIG. 11.

Figure 11:
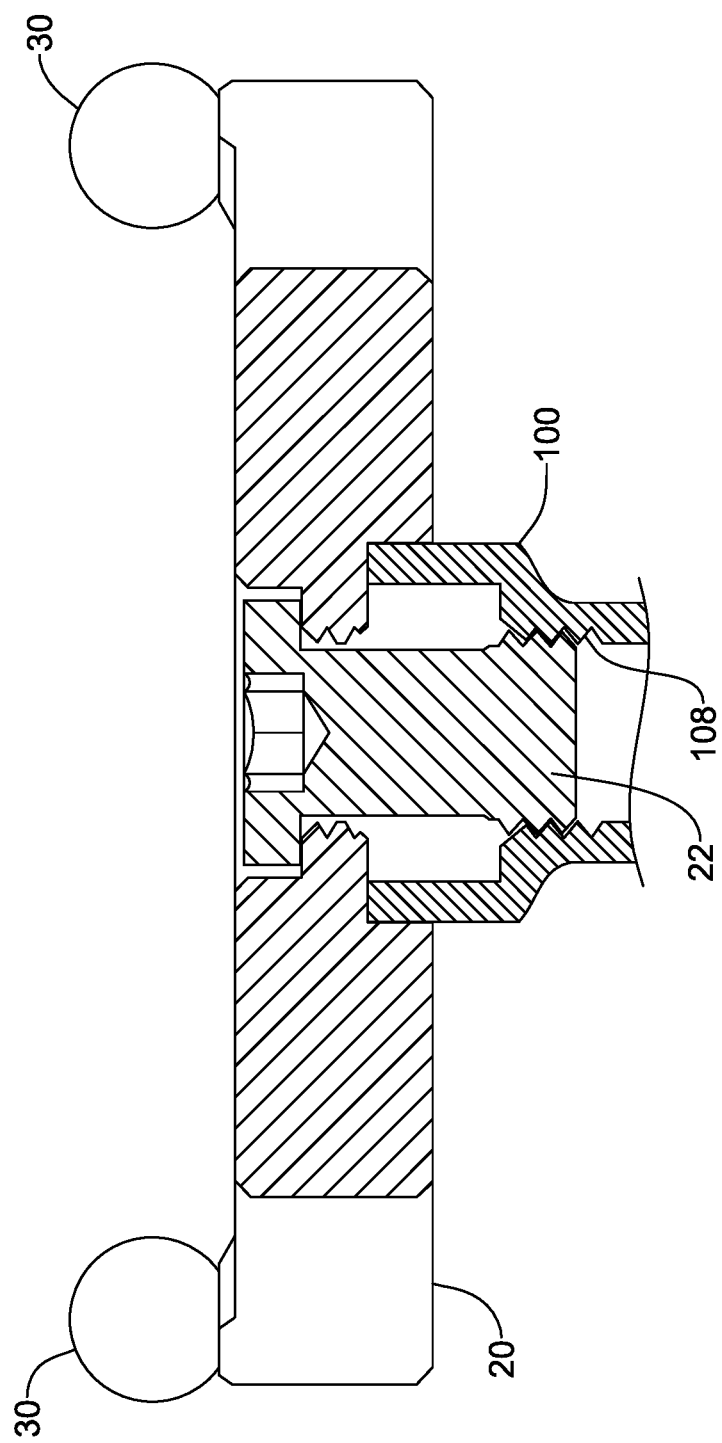
FIG. 11 illustrates a cutaway view of the reference array coupled to the adapter.

FIG. 11. illustrates a cross section view of a reference array 20 coupled to a reference array coupler 108. The illustrated connection is made via a screw fastener 22 that mates with corresponding screws of the reference array coupler 108. In addition, the figure illustrates that the proximal end of the adapter 100 can at least partially fit within the reference array 20. Such a fitting can resist the reference array from rotating with respect to the adapter 100. The illustrated reference array 20 has a width and length extending perpendicular to a long axis of the adapter 100 while the thickness of the reference array 20 is parallel to the adapter 100 when the reference array 20 is coupled to the adapter 100. Likewise, based on the connection between the adapter 100 and the receiver assembly 70, the width and length of the reference array 20 can extend perpendicular to a long axis of the receiver assembly 70 (e.g., the axis along which the arms of the receiver assembly 70 extend) and the thickness of the reference array 20 is parallel to the long axis of the receiver assembly 70 when the reference array 20 is coupled to the adapter 100 and the adapter 100 is coupled to the receiver assembly 70.

Returning to FIG. 9, operation 930 includes adjusting an angle of the receiver assembly 70 with respect to the bone anchor 60. The adjusting can simultaneously adjust an angle of the adapter 100 with respect to the bone anchor 60. The adjusting can be to move the reference array 20 from a position better for use during surgical navigation (e.g., because the reference array 20 is more visible to a navigation camera system or less likely to be obscured during a procedure). The adjusting can include moving the reference array 20, which causes the adapter 100 to move due to the rigid connection with the reference array 20, which causes the receiver assembly 70 to move relative to the bone anchor 60 due to their movable connection. The adjusting can include one, two, or three of pitching, rolling, and yawing the reference array with respect to the bone anchor 60.

Figure 12:
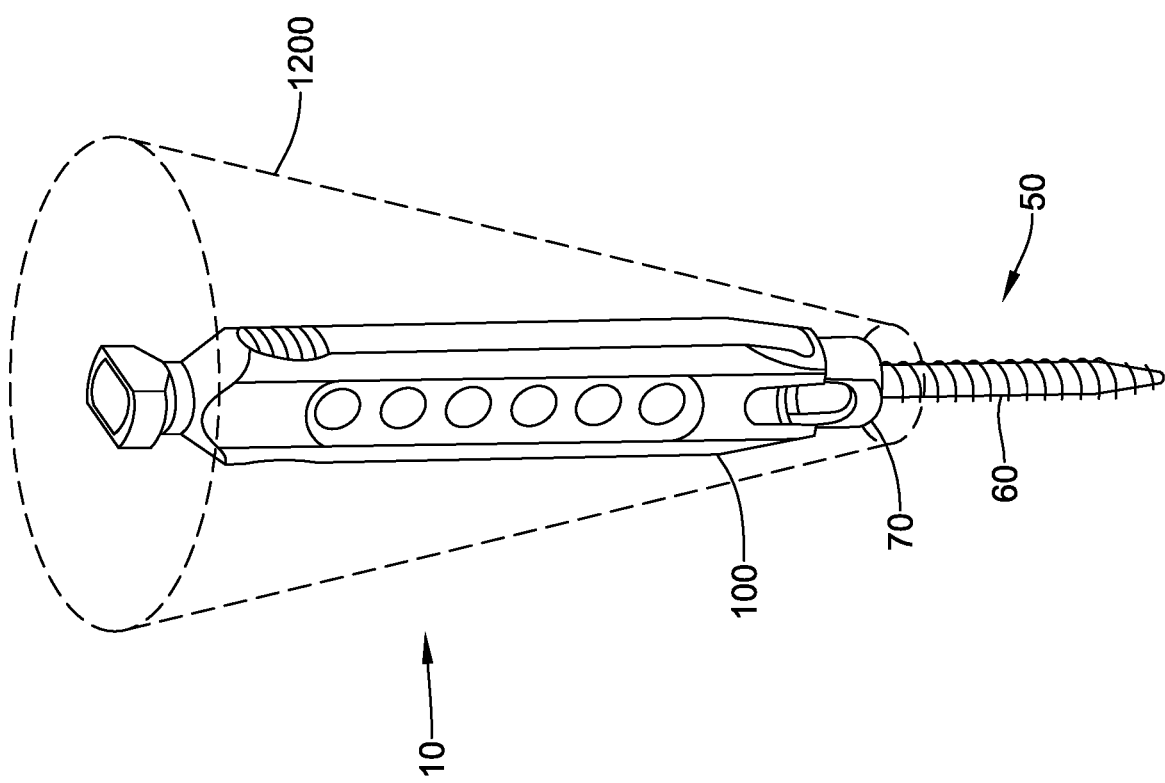
FIG. 12 illustrates a cone of angulation of an adapter coupled to a bone anchor assembly.

FIG. 12 illustrates an example cone of angulation 1200 for the apparatus 10. The cone of angulation 1200 can represent an amount of movement of the adapter 100 afforded by the connection between the adapter 100 and the receiver assembly 70, which has a movable relationship with the bone anchor 60.

Returning to FIG. 9, operation 940 includes advancing a channel engager 150 of the adapter 100 into a channel 76 of the receiver assembly 70, thereby locking an angle of the receiver assembly 70 with respect to the bone anchor 60. The technique for advancing can vary depending on the configuration of the channel engager 150. In the examples illustrated above, the channel engager 150 is able to be advanced or retracted via a driver 160 that pushes or pulls on the channel engager 150. In the illustrated configuration, the driver 160 acts as a leadscrew that transfers rotation energy imparted at a proximal end of the driver (e.g., via a screwdriver) into linear motion that moves the driver and causes the channel engager 150 to move. Advancing the channel engager 150 can include causing the driver 160 to push the channel engager shaft 152 such that the channel engager bar 154 (or other engagement element) advances into the channel 76 and contacts one or more components of the bone anchor assembly 50. The advancing can be configured to achieve or further strengthen a rigidity of a connection between the receiver assembly 70 and the adapter 100. For instance, the advancing can cause the channel engager 150 (e.g., the bar 154 thereof) to contact a component of the bone anchor assembly 50 and urge the adapter 100 upward (e.g., proximally). The upward urging can cause a proximal end of a flat of the one or more tabs 216 to abut a proximal end of the tool engager 72 and increase a rigidity of the connection by taking up play in the connection. In addition or instead, the advancing of the channel engager can cause resistance in the movement of the receiver assembly 70 relative to the bone anchor 60. For instance, the advancing of the channel engager 150 can push the collet 78 downward (distally) such that the relationship between the collet 78 and the receiver assembly 70 and the bone anchor 60 resists movement of the receiver assembly 70 relative to the bone anchor 60. Examples of the channel engager 150 in an advanced state are shown in FIGS. 13-15.

Figure 13:
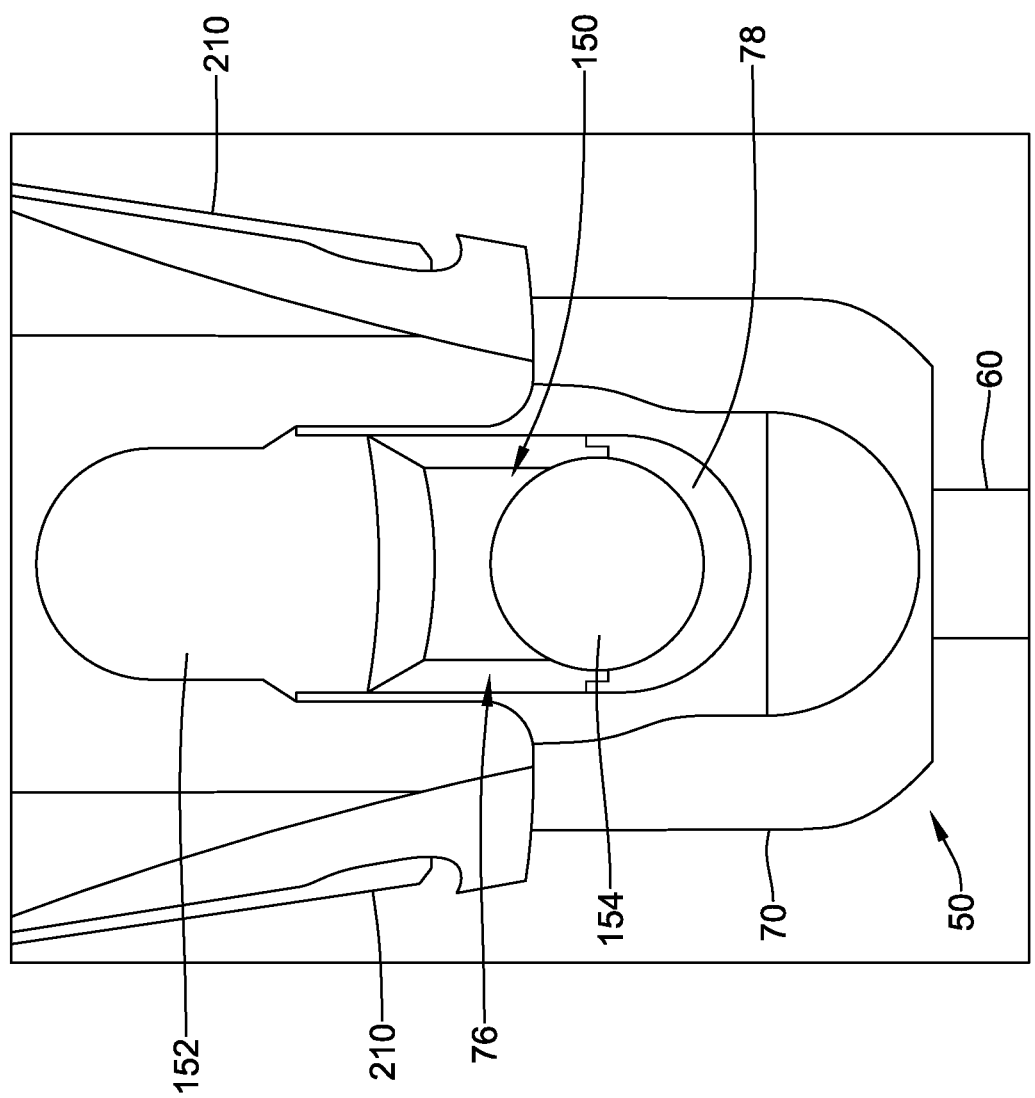
FIG. 13 illustrates a view of the adapter coupled to the bone anchor assembly with a channel engager bar deployed into a channel of the bone anchor assembly.

FIG. 13 illustrates an example channel engager 150 advanced into the channel 76 of the receiver assembly 70. Here, the channel engager 150 is in contact with the collet 78 after the channel engager drives the collet 78 into such a position that the collet 78 resists movement of the receiver assembly 70 relative to the bone anchor 60.

Figure 14:
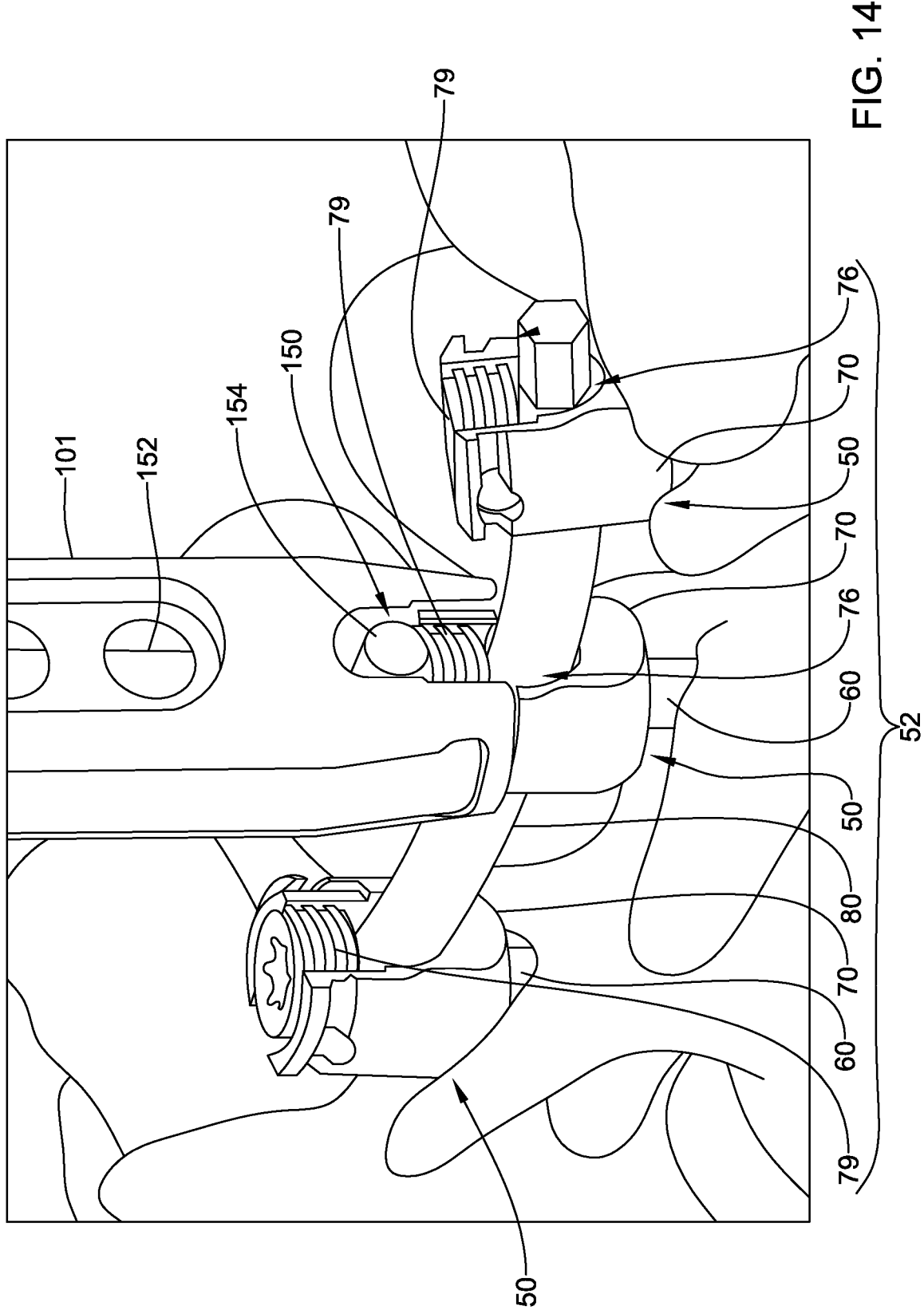
FIG. 14 illustrates the adapter coupled to a receiver assembly of a construct lacking a set screw.

FIG. 14 illustrates an example channel engager 150 advanced toward a bone anchor assembly 50 of a construct 52 that includes multiple bone anchor assemblies 50 linked by a rod 80. The rod 80 is disposed in channels 76 of multiple bone anchor assemblies 50 and held in place by set screws 79. Here, the channel engager 150 is sufficiently advanced that the bar 154 is in contact with a set screw 79. Depending on the arrangement of the bone anchor assemblies 50, the set screw 79 may cause the rod 80 to advance collets to fix the relationship between the receiver assemblies 70 and the bone anchors 60. In an example, the construct 52 is a preexisting construct from a prior surgery and the current surgery is a revision surgery.

Figure 15:
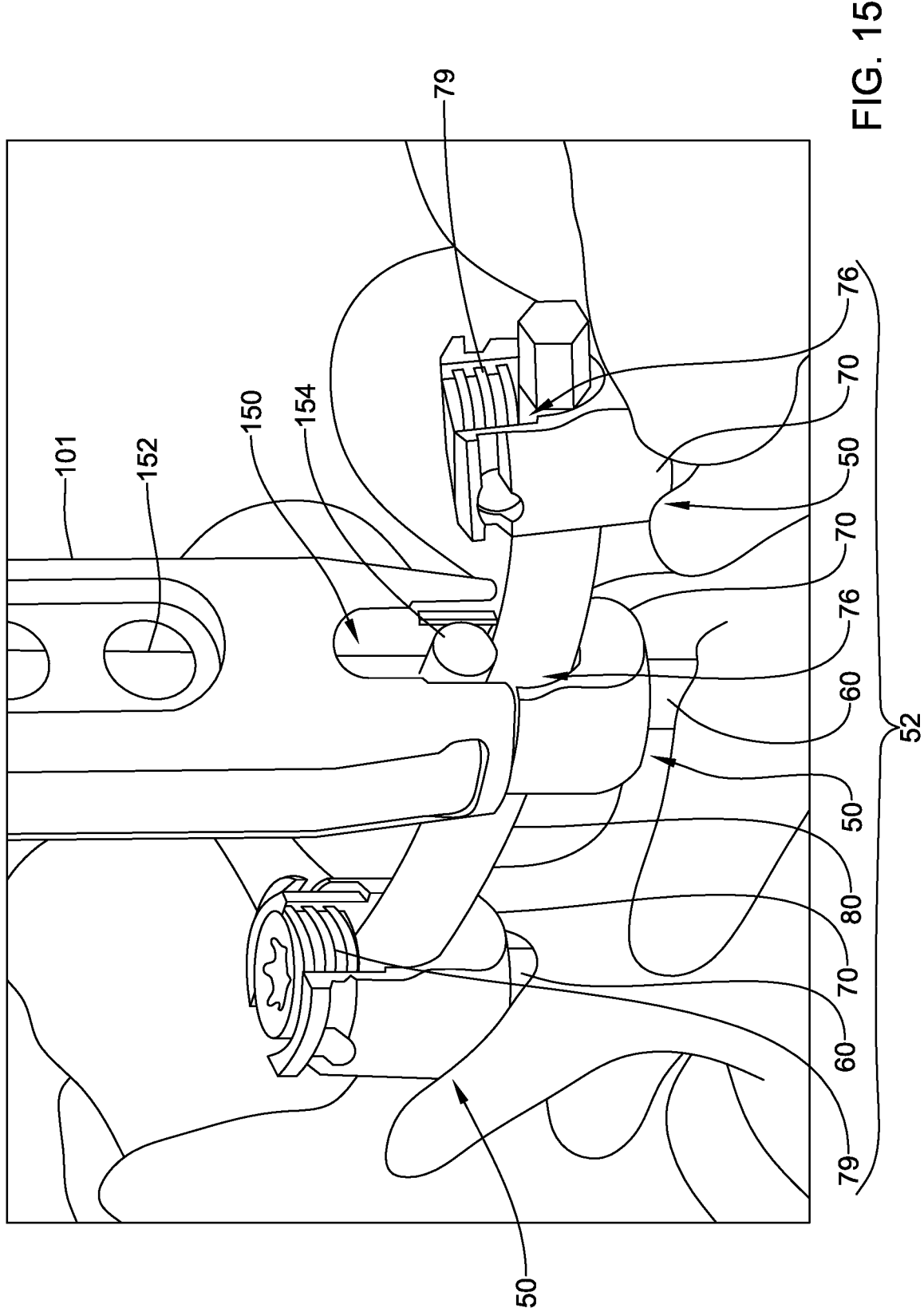
FIG. 15 illustrates the adapter coupled to a receiver assembly of a construct having a set screw.

FIG. 15 illustrates an example channel engager 150 in contact with a rod 80 of a construct 52 that includes multiple bone anchor assemblies 50 linked by the rod 80. The construct 52 is similar to the one in FIG. 14 except, here, the bar 154 is directly in contact with the rod 80 rather than a set screw.

Returning to FIG. 9, operation 950 includes uncoupling the adapter 100 from the receiver assembly 70. How the uncoupling is accomplished can vary depending on how the adapter 100 was coupled to the assembly 70. In an example, the uncoupling includes retracting the channel engager 150, such as by driving the driver 160 in reverse to cause the driver 160 to pull the channel engager 150 distally. Depending on the arrangement of the adapter, the receiver assembly 70 may need to be removed to access the driver 160. In an example, the uncoupling includes pressing in on the one or more arm interfaces 214 to cause the distal ends of the arms 210 to swing outward causing the tabs 216 to withdraw from the tool engagers 72 of the receiver assembly 70. While the tabs 216 are out of the tool engagers 72, a user can pull the adapter 100 upward to free the receiver assembly 70 from the opening 106.

Operation 960 can include connecting the receiver assembly 70 with another receiver assembly 70 via a rod 80. For example, the operation 960 can include implanting another bone anchor assembly 50 having the another receiver assembly 70 (e.g., using the benefit of surgical navigation provided by the array 20). After the implanting, the rod 80 can be disposed in the channels 76 of the two or more receiver assemblies 70 to be connected. The rod 80 can then be tightened in place by a set screw 79. The resulting construct 52 can be similar to the construct shown in FIG. 14.

Figure 16:
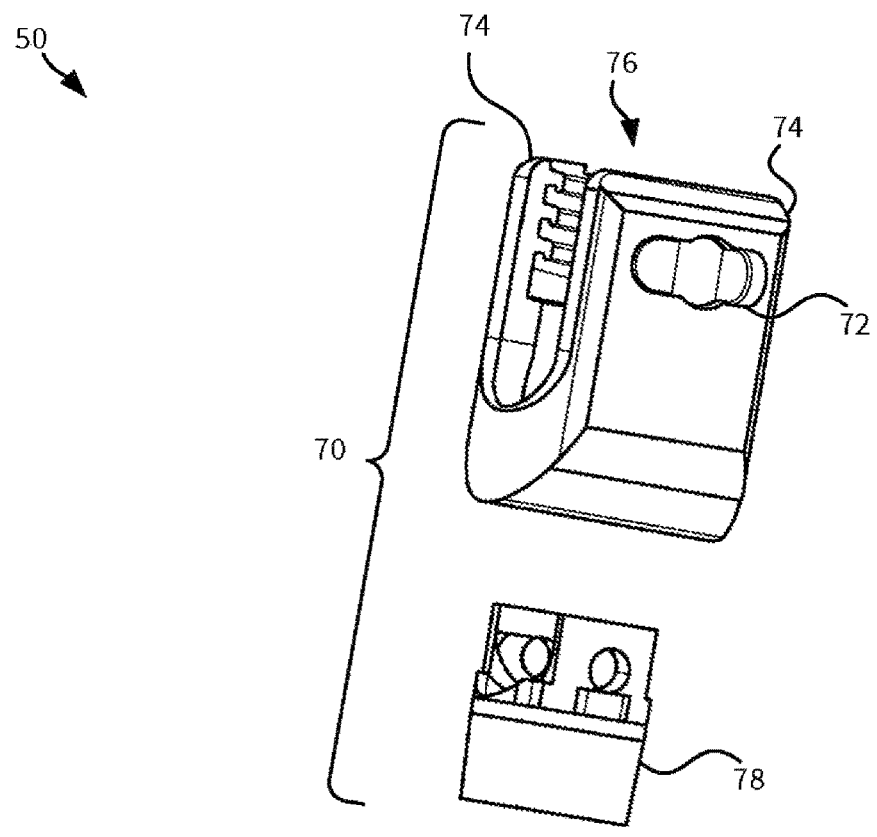
FIG. 16 illustrates an exploded view of an example bone anchor assembly.
Figure 16:
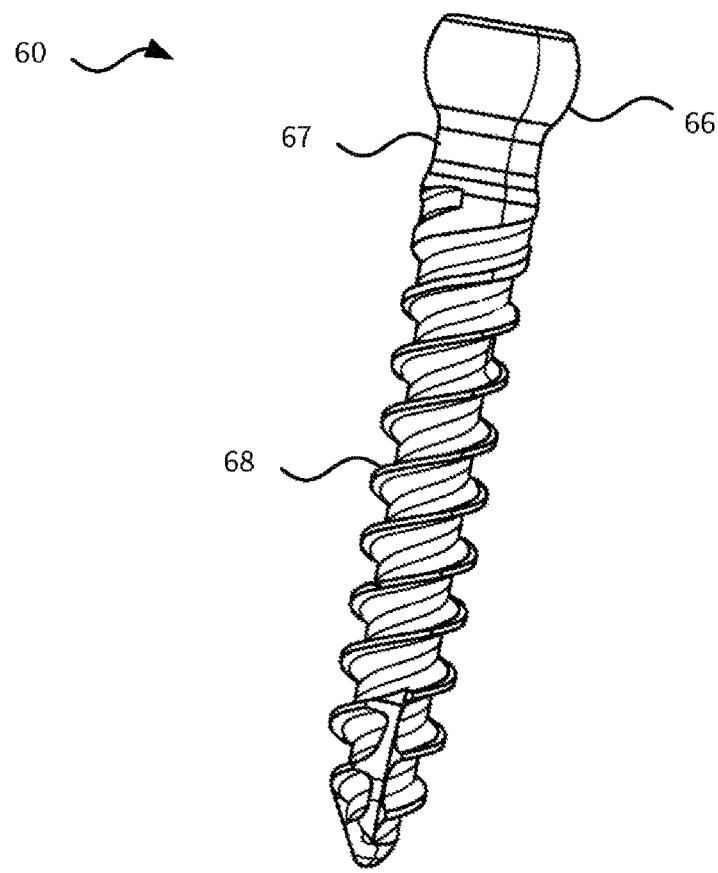

FIG. 16 illustrates an exploded view of an example bone anchor assembly 50. The figure and its description are based on U.S. Pat. No. 8,986,349, which was previously incorporated herein by reference. Other implementations of bone anchor assemblies 50 are possible.

The bone anchor assembly 50 includes a bone anchor 60 and a receiver assembly 70. The bone anchor assembly 50 can be constructed form a suitable material, such as one or more metals (e.g. titanium or stainless steel).

The bone anchor 60 is configured to attach securely within a bony structure (e.g. pedicle of a vertebra) and to allow the receiver assembly 70 to provisionally lock into position relative to the bone anchor 60 after placement of the bone anchor 60 within a bony structure. The receiver assembly 70 and bone anchor 60 are configured to engage with full polyaxial motion. The receiver assembly 70 and bone anchor 60 can also be provisionally locked (e.g., fixed relative to each other prior to final capture and locking of a spinal rod into the receiver). This versatile engagement between the receiver assembly 70 and bone anchor 60 provides both the ease of positioning and rod placement associated with polyaxial screws and the ability to leverage the bone anchor 60 to manipulate the vertebral body.

The bone anchor 60 of the bone anchor assembly 50 includes a shank 67, a body, and a capture structure 66. At least one helically-wound bone implantable thread 68 extends radially from the body and functions to secure the placement of the bone anchor 60 within a bony structure. The capture structure 66 includes at least one tool engaging feature (e.g., one or more indentations configured to receive a screwdriver) that can be used, for example, to engage and attach various tooling for aligning and advancing the bone anchor 60 into a bony structure. The generally spherical shape of the capture structure 66 allows the capture structure 66 to articulate within the collet 78 to achieve the polyaxial motion between the bone anchor 60 and the receiver assembly 70.

The receiver assembly 70 is configured to receive an elongate structure (e.g. a rod) within a channel 76 and secure the rod within the channel 76. Once the receiver assembly 70 and bone anchor 60 are securely oriented in the desired orientation and the rod is captured in the receiver assembly 70, a set screw or another structure can be engaged to lock the rod in the receiver assembly 70.

The receiver assembly 70 is typically provided in an assembled state and includes a collet 78. The receiver assembly has a generally U-shaped appearance with a generally cylindrical inner profile and a faceted outer profile. A base with a pair of upstanding receiver arms 74 form a U-shaped cradle which define the channel 76. Receiver assemblies 70 may be provided in a variety of dimensions depending on the size and shape of the rod that it will be in secured frictional engagement with.

The arms 74 typically have at least one helically-wound guide and advancement structure at least partially situated along their internal walls beginning from the top surface of the receiver arms 74. The guide and advancement structure are configured to mate with at least one exterior helically-wound structure (e.g., a set screw).

Figure 17:
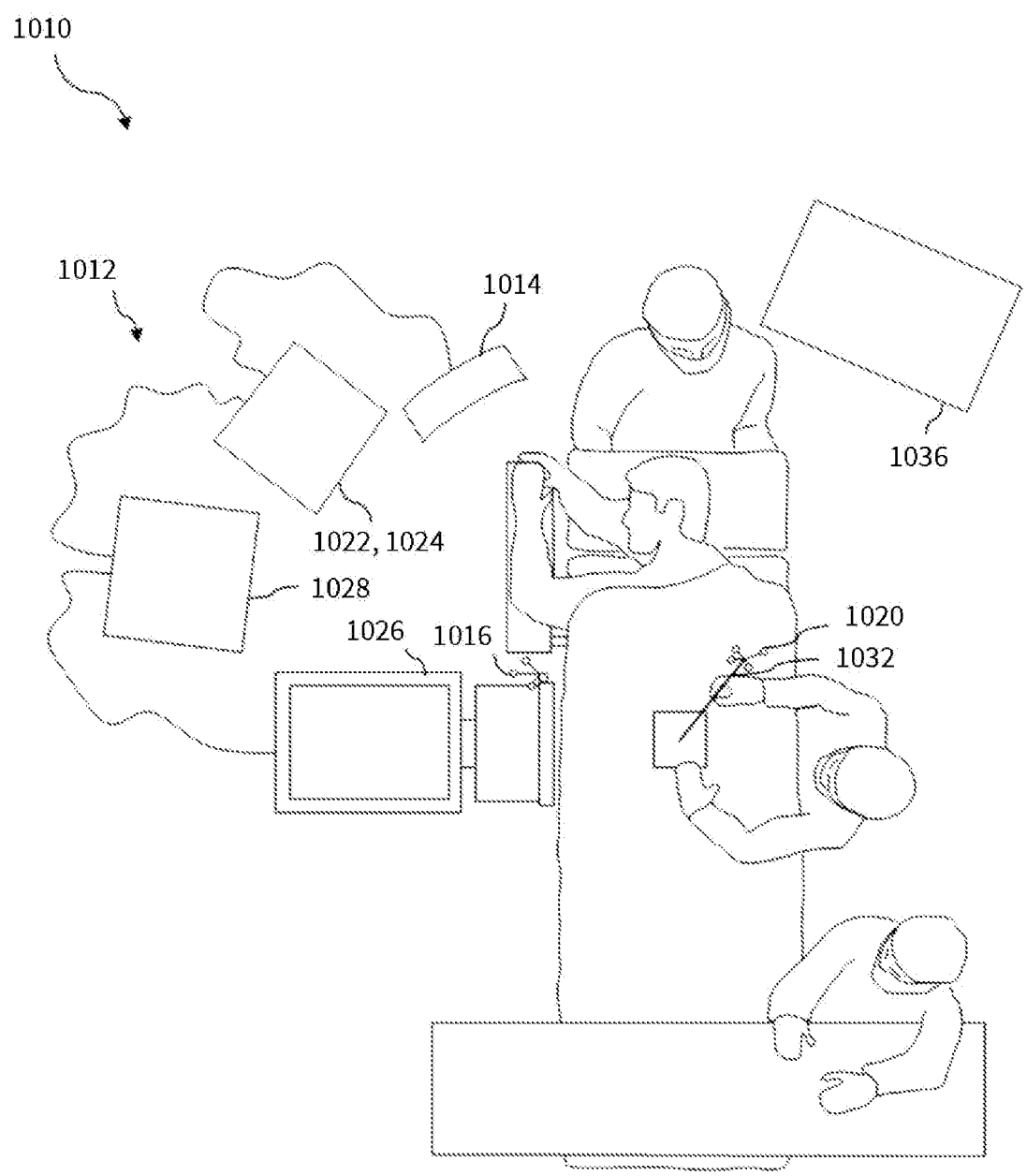
FIG. 17 illustrates an example system.

FIG. 17 illustrates an example system 1010 with which examples described herein can be used. This figure and its description are based on U.S. Pat. No. 9,510,771, filed Oct. 28, 2011, which is incorporated herein by reference in its entirety for any and all purposes. Examples described herein can be used with other kinds of systems.

The illustrated surgical tracking system 1010 including a position tracking system 1012 and at least one surgical object to be tracked. Preferably, the position tracking system 1012 includes an infrared (IR) position sensor 1014 (also referred to as an "IR camera"), an IR-reflective tracking array 1016 mounted on an intraoperative imaging system 1018, an IR-reflective tracking array 1020 mountable to each surgical object to be tracked and a feedback and control device comprising a control unit 1022 and a display 1024. The control unit 1022 has position tracking software and C-arm video import capabilities and is communicatively linked to the display 1024 so that information relevant to the surgical procedure may be conveyed to the user in a meaningful manner. By way of example, the relevant information includes, but is not limited to, spatial positioning data (e.g., translational data in the x, y, and z axes and orientation/rotational data) acquired by the IR position tracking sensor 1014. The intraoperative imaging system 1018 may be any commercially available C-arm fluoroscope 1026 communicatively linked to a C-arm display 1028 with an IR-reflective tracking array 1016 attached, for example, to the signal receiver.

Examples herein can facilitate monitoring the location and orientation of surgical access instruments which can aid in both the insertion and positioning of the surgical access instruments themselves, as well as aiding in the later insertion of instruments and/or implants through the surgical access instruments. In another example, tracking the location of surgical instruments within the surgical field may be accomplished with significantly decreased reliance on intraoperative imaging. In yet another example, the present invention may be used in conjunction with, or integrated into, a neuromonitoring system for assessing one or more of nerve proximity (and/or nerve directionality) and pedicle integrity, among other functions. In still another example, the present invention may facilitate safe and reproducible pedicle screw placement by monitoring the trajectory of various surgical instruments used during pilot hole formation and/or screw insertion. While the above examples are described in more detail below, it is expressly noted that they are set forth by way of example and that the present invention may be suitable for use in any number of additional surgical actions where tracking the 3D location of surgical instruments and implants within the surgical field and decreased exposure to x-ray radiation are desired. Accordingly, it will be appreciated then that while the surgical tracking system is generally discussed herein as being attached to instruments such as dilating cannulas, tissue retractors, C-arms, pedicle access tools, etc., other instruments may be substituted depending on the surgical procedure being performed and/or the needs of the surgeon.

Any of the features or attributes of the above described embodiments and variations can be used in combination with any of the other features and attributes of the above described embodiments and variations as desired. Various modifications, additions and other alternative embodiments are possible without departing from the true scope and spirit. The embodiments presented herein were chosen and described to provide an illustration of various principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. An apparatus comprising:
   a reference array;
   a bone anchor;
   a receiver assembly coupled to the bone anchor and including:
     at least two receiver arms defining a channel therebetween configured to receive a spinal rod; and
     one or more tool engagers; and
   an adapter axially locked with the receiver assembly having:
     a body, wherein the body defines a cavity;
     a channel engager slidably coupled to the body and housed within the cavity, wherein the channel engager is configured to engage within the channel;
     a channel engager pin removably coupled to the channel engager, the channel engager pin configured to engage a track in the body to facilitate guiding the channel engager down the track;
     one or more receiver assembly engagers pivotably coupled to the body and configured to releasably couple with the one or more tool engagers;
     a proximal end coupled to the reference array; and
     a distal end coupled to the receiver assembly,
     wherein the one or more receiver assembly engagers are coupled to the body at the proximal end and configured to pivot when an arm of each of the one or more receiver assembly engagers engages an arm spring.

2. The apparatus of claim 1, wherein the channel engager includes:
   a channel engager shaft having a distal end; and
   a bar having a length that extends perpendicularly from the distal end of the channel engager shaft.

3. The apparatus of claim 2, wherein the bar defines a flat distal surface.

4. The apparatus of claim 2, wherein the bar defines a convex distal surface.

5. The apparatus of claim 2, wherein the bar mimics a shape and diameter of a spinal rod.

6. The apparatus of claim 1, wherein the one or more receiver assembly engagers each include:
at least one tab extending toward a central axis of the adapter, the tab having a ramped distal surface.

7. The apparatus of claim 6,
wherein the adapter includes a driver configured to advance the channel engager into the channel and withdraw the channel engager from the channel.

8. An apparatus comprising:
a proximal end having a reference array coupler;
a distal end defining an opening configured to receive a receiver assembly;
a body, wherein the body defines a cavity;
a channel engager slidably coupled to the body and housed within the cavity, wherein the channel engager is configured to engage within a channel formed by the receiver assembly;
a channel engager pin removably coupled to the channel engager, the channel engager pin configured to engage a track in the body to facilitate guiding channel engager down the track; and
one or more receiver assembly engagers pivotably coupled to the body and configured to releasably engage with the receiver assembly,
wherein the one or more receiver assembly engagers are coupled to the body at the proximal end and configured to pivot when an arm of each of the one or more receiver assembly engagers engages an arm spring.

9. The apparatus of claim 8,
wherein each arm is biased into a locked position; and
wherein each arm includes one or more tabs configured to fit within one or more tool engagers of the receiver assembly.

10. The apparatus of claim 8,
wherein the channel engager includes a channel engager shaft having a channel engager bar extending perpendicular to a length of the channel engager shaft; and
wherein the channel engager bar is a portion of the channel engager that engages within the channel.

11. The apparatus of claim 8, further comprising:
wherein a distal end of the channel engager bar has a flat or convex distal surface.

12. The apparatus of claim 11, wherein the channel engager bar mimics a shape and diameter of a spinal rod.

13. The apparatus of claim 10, further comprising:
a driver configured to advance the channel engager into the channel and withdraw the channel engager from the channel.

14. The apparatus of claim 13,
wherein the driver is configured as a lead screw configured to translate rotational force applied to the driver to advance or withdraw the channel engager.

15. A method comprising:
coupling an adapter with a receiver assembly that is coupled to a bone anchor disposed in bone, wherein the coupling includes:
engaging an interface of an arm pivotably coupled to a body of the adaptor such that the arm compresses a biasing member coupled to the body, wherein the arm is pivotably coupled to the body at a proximal end of the adaptor;
releasing the interface to pivot the arm such that one or more tabs of the arm of the adapter are disposed within one or more tool engagers of the receiver assembly;
coupling a reference array to a proximal end of the adapter; and
adjusting an angle of the receiver assembly with respect to the bone anchor,
wherein the adjusting simultaneously adjusts an angle of the adapter with respect to the bone anchor,
wherein the adapter includes a channel engager slidably coupled to the body and housed within the cavity, wherein the channel engager is configured to engage within the channel, and
wherein the adapter includes a channel engager pin removably coupled to the channel engager, the channel engager pin configured to engage a track in the body to facilitate guiding channel engager down the track.

16. The method of claim 15, wherein releasing the interface includes:
pushing a ramped distal surface of the one or more tabs onto a proximal end of the receiver assembly, thereby causing the distal end of the arm to be pushed outward and then fall into the one or more tool engagers of the receiver assembly.

17. The method of claim 15, further comprising:
after adjusting the angle, advancing a channel engager of the adapter into a channel of the receiver assembly, thereby locking an angle of the receiver assembly with respect to the bone anchor.

18. The method of claim 15, further comprising:
advancing the channel engager of the adapter toward a channel of the receiver assembly such that the channel engager contacts a set screw or rod disposed in the receiver assembly.

19. The method of claim 15,
wherein the method is performed during a revision spinal surgery; and
wherein the bone anchor was placed during a prior spinal surgery.

20. The method of claim 15, wherein the method further comprises:
uncoupling the adapter from the receiver assembly; and
connecting the receiver assembly with another receiver assembly via a rod.

* * * * *